United States Patent [19]
Bergersen

[11] Patent Number: 4,799,884
[45] Date of Patent: Jan. 24, 1989

[54] EXPANSION/BUCCAL SHIELD APPLIANCE

[76] Inventor: Earl O. Bergersen, 950 Green Bay Rd., Winnetka, Ill. 60093

[21] Appl. No.: 116,672

[22] Filed: Nov. 4, 1987

[51] Int. Cl.$^4$ .............................................. A61C 3/00
[52] U.S. Cl. ........................................................ 433/6
[58] Field of Search ............................ 433/6; 128/136

[56] References Cited

U.S. PATENT DOCUMENTS

| | | | |
|---|---|---|---|
| 3,510,946 | 5/1970 | Kesling | 433/6 |
| 4,055,895 | 11/1977 | Huge | 433/6 |
| 4,253,828 | 3/1981 | Coles et al. | 433/6 |
| 4,413,978 | 11/1983 | Kurz | 433/6 |

Primary Examiner—John J. Wilson
Attorney, Agent, or Firm—Hill, Van Santen, Steadman & Simpson

[57] ABSTRACT

An orthodontic appliance is provided which has a buccal shield, an occlusal plate, a lingual flange for the incisors and slots for receiving the posterior teeth. The posterior segment of the appliance is preformed wider than the patient's lateral posterior teeth spacing and the slots are open lingually to permit the patient's tongue to press against the lingual surface of the posterior teeth to cause them to expand buccally. The slots are angled posteriorly to cause the posterior teeth to move distally.

14 Claims, 1 Drawing Sheet

EXPANSION/BUCCAL SHIELD APPLIANCE

BACKGROUND OF THE INVENTION

1. Field of the Invention:

The invention relates to tooth positioning appliances, and in particular to an appliance to be used with deciduous dentition or mixed dentition to expand the posterior segments.

2. Description of the Prior Art:

Over crowding of the teeth, particularly the anterior teeth is one condition which can be corrected with orthodontic treatment. Oftentimes metallic bands and wires are used in the permanent dentition stage to provide the desired spacing. There have also been provided devices such as my prior device disclosed in U.S. Pat. No. 4,139,944 in which a plastic removable positioner is provided for use in correcting certain conditions in a permanent or mixed dentition stage.

SUMMARY OF THE INVENTION

The present invention provides a U-shaped appliance which may be used for the upper and lower arches with a connecting isthmus or plate that engages the occlussal surfaces of the teeth. The appliance can be used for either deciduous teeth only or can be used for mixed dentition or permanent dentition. The mixed dentition would consist of permanent upper and lower incisors (central and lateral incisors) and first permanent molars, deciduous canines, deciduous first molars and deciduous second molars. The lateral spacing of the inter-canine, first deciduous molar-to-molar and the second deciduous molar-to-molar would be expanded for example by about 7 mm from their normal position and the mesial-distal canine-to-canine distance would be increased for example by about 4 mm from its normal distance.

Individual slots, open lingually, are provided in the appliance for the posterior teeth and because of the early stage of development of the patient's mouth at the age up to mixed dentition, the posterior teeth will move to the expanded position of the preformed appliance to provide increased spacing for the incisors.

DESCRIPTION OF THE PREFERRED EMBODIMENTS

Figure 1:
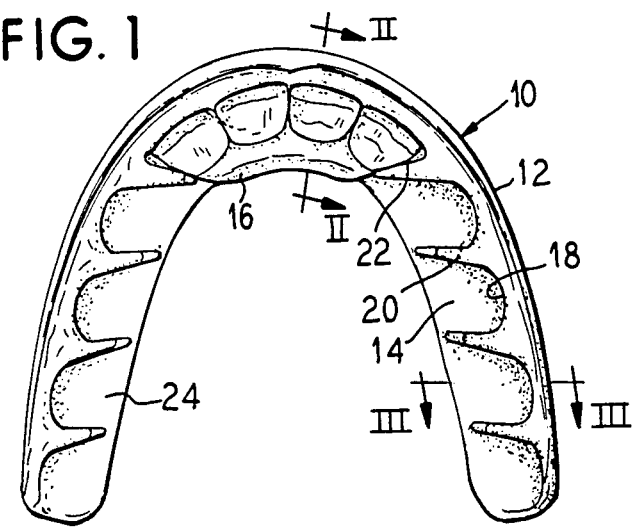
FIG. 1 is an occlussal view of an orthodontic appliance embodying the principles of the present invention.
Figure 2:
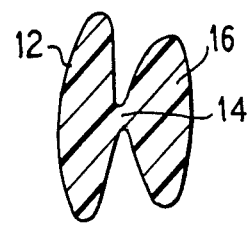
FIG. 2 is a side sectional view of the appliance taken generally along the line II—II of FIG. 1.
Figure 3:
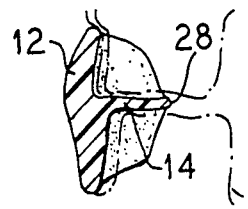
FIG. 3 is a side sectional view of the appliance taken generally along the line III—III of FIG. 1.
Figure 4:
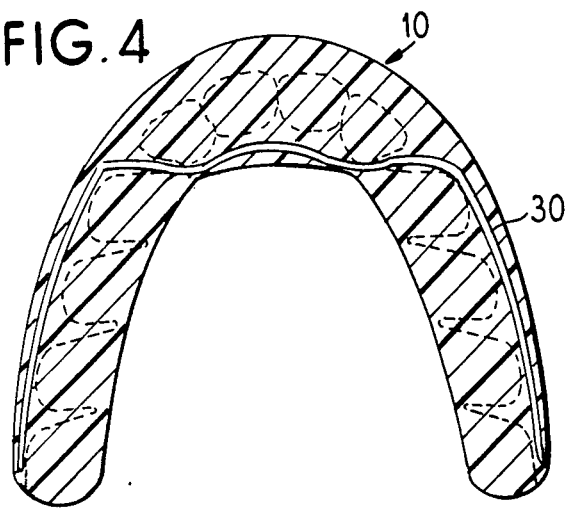
FIG. 4 is a sectional view through the occlussal plate area of the appliance and showing an embedded wire.
Figure 6:
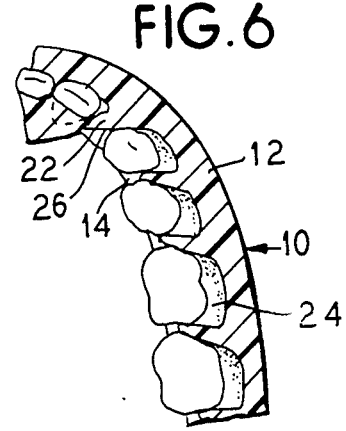
FIG. 6 is a partial sectional view of an appliance without a wire.

In FIG. 1 there is illustrated an appliance generally at 10 which is generally U-shaped in occlussal or plan view and which includes an outer buccal flange 12 which overlies the buccal surface of at least one of the upper or lower rows of the patient's teeth. Projecting lingually of the buccal shield 12 is an occlussal plate or shelf 14 which is to engage an occlussal surface of the patient's teeth. A lingual flange 16 is provided at an anterior bight portion of the U-shaped appliance to overlie a lingual surface of at least one of an upper or lower set of central and lateral incisors I. The lingual flange 16 terminates prior to the canines C so that the patient's tongue will be free to engage the lingual surface of the posterior teeth (canines and molars M). The buccal shield 12 holds the cheeks and lips away from the buccal and labial surfaces of the patient's teeth.

The appliance is a preformed or custom-made device fabricated of a molded resilient material such as plastic that conforms to the anterior teeth (central and lateral incisors) and, the buccal shield 12 is spaced laterally away from the posterior teeth. Thus, the force of the tongue against the posterior teeth causes these teeth to move buccally to gain extra room for the patient's crowded or potentially crowded teeth.

A lingual surface 18 of the buccal shield is notched in that it has lingually extending projections 20 extending therefrom, the projections 20 being positioned to project into the interproximal spaces between each of the posterior teeth and a wedge shaped projection 22 is provided between the canines and lateral incisors. The projections 20 are angled anteriorly and lingually from their points of attachment at the buccal shield to thereby define a buccally and posteriorly directed slot or pocket 24 for receiving each of the posterior teeth. The slanting of the projections encourages each buccal tooth to assume an expanded position while gaining space anteriorly between the canine and the lateral incisors where the space can be used for the elimination of crowding in the anterior segment, especially in the lateral-canine area. Preferably, the expansion of the buccal shield allows for approximately 1-20 mm of expansion between the canines in the upper the lower arches as well as approximately 1-20 mm of lateral expansion between each of the molars. Expansion may be provided for the anterior segment if desired or needed, but in some instances no anterior segment expansion would be required.

The wedged shaped projection 22 between the lateral incisors and the canine causes the canine to drift distally along a distal surface 26 of the wedge to assume a more expanded but slightly distal position. As each tooth distal of the canine is expanded, it in turn migrates slightly distally or at least does not move mesially as it expands. In this way, the excess space created by the posterior expansion ends up in the lateral-canine area. If the canine is missing, the deciduous first molar will still be guided distally by its mesial interproximal projection 20.

Preferably the appliances are preformed in varying sizes to accommodate 1.5 mm variations in accumulative mesial-distal widths of the six permanent anterior teeth in the maxilla. The measurement can be taken in the maxilla from the distal surface of the left to right incisor or in a similar way in the mandible. Approximately thirteen sizes will accommodate about 95% of the population variations. The expansions in the posterior segments are predicated upon the normal statistically expected arch widths in each tooth area (canine, first and second deciduous molars and first permanent molars) together with an additional 7 mm in arch width of each tooth area. The appliances may also be custom made to fit individual patients.

The anterior segment may be increased vertically to a greater extent than the posterior in order to decrease the vertical overbitting anteriorly and to encourage the posterior teeth to obtain more eruption than normally expected as is described in greater detail in my prior U.S. Pat. No. 3,939,598. The anterior segment may be decreased to correct open bite or the anterior and posterior segments may be of equal thickness.

The lingual isthmus or occlussal shelf 14 extends lingually, but not completely to the lingual surface of the preexpanded position of the posterior teeth otherwise it would prevent the tongue from expanding the teeth properly. That is, the shelf has a lingual edge 28 which is to be positioned buccally of the lingual edge of the buccal teeth. However, if the shelf extends beyond where it will match the lingual surface of the posterior teeth in their fully expanded position, it can be trimmed off slightly.

The appliance can be made for an all deciduous dentition, mixed dentition or all permanent dentition. The only differences would be the length of the posterior segments and the positions of the interproximal projections. The appliance can also be premade for any degree of expansion as well, be it more or less than 7 mm.

The lingual surface of the buccal shield will be slightly more buccal in the maxilla than the mandible in order to prevent buccal-lingual cross-bites from occurring. It is possible, however, to adjust this by trimming on the inside lingual surface if it is desirous to have one tooth moved more buccally than another, particularly in the over correction of a cross-bite condition.

The expanded result after wearing this appliance will match the expansion pre-set into the expanded appliance that has all posterior sockets present as well as a lingual vertical flange present lingual to these posterior teeth which is the type such as that described in my prior patent referred to above. Thus, the patient can wear that type of appliance as a retaining appliance as well as to better control the posterior occlusion after satisfactory expansion with the present invention has been obtained.

The material of the present appliance 10 can be of any degree of hardness or softness, whichever is found to respond better with any particular patient's musculature. There may be several degrees of hardness of material as an option for certain types of cases, be it a constricted mouth with heavy powerful buccinator and masseter muscles which might require a harder, less resilient material, while a more placid, softer, weaker musculature might be more comfortable with a softer material.

It also may be beneficial to start out with an appliance that has minimal expansion and after sufficient expansion has been obtained with this appliance, the next wider and perhaps harder material might be used to gain greater expansion. This could continue until sufficient adequate expansion has been obtained for the patient's degree of crowding. The appliance is removable so the patient's use is passive, but it would be preferable for the patient to use the device as many hours each night and day as possible to gain adequate expansion.

Figure 5:
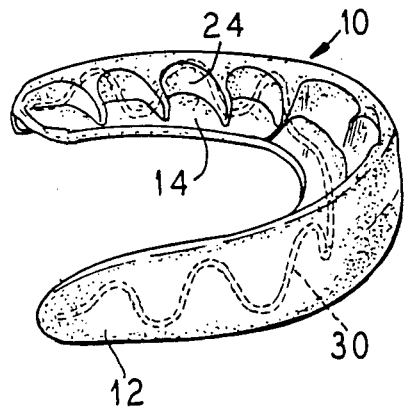
FIG. 5 is a side prespective view of an appliance incorporating an embedded wire.
Figure 7:
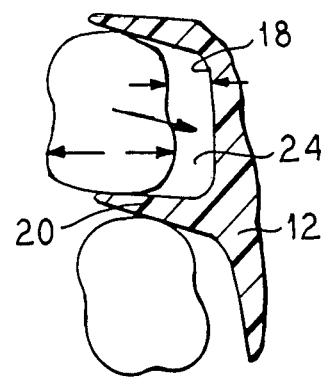
FIG. 7 is an enlarged partial view of a posterior portion of the appliance showing the interaction of the teeth with the interproximal projections.

It also may be preferable to include a wire member 30 molded in the interior of the appliance to assist in maintaining the desired buccal expansion dimension of the appliance. The wire 30 may have a serpentine shape as best seen in FIG. 5 to permit adjustments of the appliance horizontally as well as vertically or a combination of horizontal and vertical in a compound bend.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An orthodontic appliance for expansion of at least one of the upper or lower arches in a patient comprising generally U-shaped appliance comprising:
    a buccal shield portion for overlying a labial-buccal surface of at least one of the upper or lower rows of the patient's teeth,
    an interocclusal plate extending lingually of said shield,
    a lingual flange to overlie a linual surface of the patient's incisors, and
    a plurality of projections defining tooth receiving slots therebetween extending longitudinally from said buccal flange,
        said projections being spaced to project between each of the posterior teeth of the patient.

2. An orthodontic appliance according to claim 1, wherein said projections are angled anteriorly from their points of attachment to the buccal shield to guide the teeth engaged therebetween distally and buccally.

3. An orthodontic appliance according to claim 1, wherein said appliance is formed of a resilient molded material and including a resilient wire member molded in the interior of said appliance to assist in retaining the shape of the appliance.

4. An orthodontic appliance according to claim 1, wherein said buccal shield overlies the buccal surface of both the upper and lower rows of the patient's teeth.

5. An orthodontic appliance according to claim 1, including a wedge shaped projection positioned between the lateral incisor and the canine to drive the canine buccally and distally.

6. An orthodontic appliance for expansion of at least one of the upper or lower arches in a patient, comprising a generally U-shaped appliance comprising:
    a buccal shield portion for overlying a labial buccal surface of at least one of the upper or lower rows of the patient's teeth,
    an interocclusal plate extending lingually of said shield, and
    a plurality of individual slots for receiving the posterior teeth of said patient,
        said slots being open lingually and being bounded on a buccal side by an anterior surface of said buccal flange, said anterior surface being spaced buccally from the buccal surface of said teeth,
    whereby, the patient's posterior teeth will be expanded buccally by the force of the patient's tongue on the posterior teeth.

7. An orthodontic appliance according to claim 6, wherein said slots include sidewalls therebetween which project lingually from said buccal shield, said sidewalls being angled anteriorly from said buccal shield to said open lingual side of said slots to additionally urge the posterior teeth distally.

8. An orthodontic appliance according to claim 6, wherein said interocclusal plate has a lingual edge which terminates buccally of a lingual surface of the posterior teeth.

9. An orthodontic appliance according to claim 8, wherein said lingual edge of said plate does not extend lingually of a lingual surface of said posterior teeth after their buccal expansion.

10. An orthodontic appliance according to claim 6, wherein said appliance is preformed.

11. An orthodontic appliance according to claim 6, wherein said appliance is custom made.

12. A method of positioning teeth comprising the steps of:

providing an orthodontic positioner of the type which is generally U-shaped in plan view and includes in at least one of the top or bottom thereof a tooth receiving trough for receiving and positioning teeth, said providing step comprising selecting a preformed positioner having in the trough or troughs therein depressions for the patient's incisor teeth and individual slots for the patient's posterior teeth, said depressions for the incisor teeth being sized at least large enough for the normal spacings of the incisors and said slots for the posterior teeth being open on the lingual side and having a buccal wall laterally spaced at a distance greater than the normal lateral spacing of the buccal surface of the posterior teeth of the patient, applying the positioner for use by a patient during at least one of a deciduous, mixed or permanent dentition stage of development, whereby such use causes the posterior teeth to expand buccally.

13. The method of claim 12, wherein said providing step includes providing a positioner having tooth receiving troughs in both the top and bottom thereof.

14. The method of claim 12, wherein said providing step includes providing a positioner wherein the slots for receiving the posterior teeth angle posteriorly.

* * * * *